US012655085B2

(12) United States Patent
Wu et al.

(10) Patent No.: US 12,655,085 B2
(45) Date of Patent: Jun. 16, 2026

(54) PREPARATION METHOD AND APPARATUS FOR METHYL METHACRYLATE

(71) Applicants:ZHEJIANG NHU COMPANY LTD., Shaoxing (CN); ZHEJIANG NHU SPECIAL MATERIALS CO., LTD., Shaoxing (CN)

(72) Inventors: Lei Wu, Shaoxing (CN); Kunpeng Cheng, Shaoxing (CN); Xueming Li, Shaoxing (CN); Runrun Hong, Shaoxing (CN); Qing'ai Shi, Shaoxing (CN); Chuang Wang, Shaoxing (CN); Guodong Huang, Shaoxing (CN); Guiyang Zhou, Shaoxing (CN)

(73) Assignees: ZHEJIANG NHU COMPANY LTD., Shaoxing (CN); ZHEJIANG NHU SPECIAL MATERIALS CO., LTD., Shaoxing (CN)

( * ) Notice: Subject to any disclaimer, the term of this patent is extended or adjusted under 35 U.S.C. 154(b) by 494 days.

(21) Appl. No.: 18/240,466

(22) Filed: Aug. 31, 2023

(65) Prior Publication Data

US 2023/0406807 A1     Dec. 21, 2023

Related U.S. Application Data

(63) Continuation of application No. PCT/CN2022/115487, filed on Aug. 29, 2022.

(30) Foreign Application Priority Data

Oct. 31, 2021    (CN) .......................... 202111278838.3

(51) Int. Cl.
| | |
|---|---|
| *C07C 67/035* | (2006.01) |
| *B01J 19/00* | (2006.01) |
| *B01J 21/06* | (2006.01) |
| *B01J 23/04* | (2006.01) |
| *C07C 69/54* | (2006.01) |

(52) U.S. Cl.
CPC ......... *C07C 67/035* (2013.01); *B01J 19/0006* (2013.01); *B01J 21/066* (2013.01); *B01J 23/04* (2013.01)

(58) Field of Classification Search
CPC ...... C07C 67/035; C07C 69/54; B01J 21/066; B01J 23/04
See application file for complete search history.

(56) References Cited

FOREIGN PATENT DOCUMENTS

| | | | |
|---|---|---|---|
| CN | 106674010 A | 5/2017 | |
| CN | 109232247 A | 1/2019 | |
| CN | 110981727 A | 4/2020 | |
| CN | 111517953 A | 8/2020 | |
| CN | 111574369 A | 8/2020 | |

OTHER PUBLICATIONS

International Search Report of PCT/CN2022/115487.

*Primary Examiner* — Sikarl A Witherspoon

(57) ABSTRACT

A method and apparatus for preparing methyl methacrylate (MMA) are provided. The method includes an aldol condensation reaction, a first distillation, a second distillation, a third distillation, a phase splitting, and a fourth distillation. Through the control of the process, the aldol condensation reaction can be performed when methyl propionate is used as the ninth material stream and formalin solution is used as the fifteenth stream material, MMA is obtained as the final product from the third material stream, and the waste with low content of residual formaldehyde is recovered from the eighth material stream.

18 Claims, 3 Drawing Sheets

PREPARATION METHOD AND APPARATUS FOR METHYL METHACRYLATE

CROSS-REFERENCE TO RELATED APPLICATIONS

This application is a continuation of international patent application No. PCT/CN2022/115487, filed on Aug. 29, 2022, which itself claims priority to Chinese Patent Application No. 202111278838.3, entitled "PREPARATION METHOD AND APPARATUS FOR METHYL METHACRYLATE" and filed on Oct. 31, 2021, the entire contents of which are incorporated herein by reference.

TECHNICAL FIELD

The present application relates to the technical field of organic synthesis, and in particular, to a method and an apparatus for preparing methyl methacrylate.

BACKGROUND

Methyl methacrylate (MMA) is a colorless, volatile, flammable liquid and has a strong spicy, a molecular formula $C_5H_8O_2$, which is an important organic chemical raw material. MMA is a monomer for preparing polymethyl methacrylate (PMMA, i.e. organic glass), and it can also be used for preparing acrylic coatings, polyvinyl chloride additives, textile emulsions, and latex plasticizers, and can be used as a second monomer for acrylic polymerization and the like. Recently, MMA has also been applied in high-tech fields such as optics, organic glass, and optical fiber.

The main industrial processes for preparing MMA include an ethylene method, an acetone cyanohydrin method, and an isobutylene oxidation method. In particular, Lucite International improved the ethylene method and provided the Alpha process, which mainly included two reaction processes: ethylene reacted with carbon monoxide and methanol under certain conditions to form methyl propionate; and methyl propionate and formaldehyde underwent aldol condensation reaction to generate MMA. This process has the advantages of mild process conditions, less corrosivity to equipment, few byproducts, high atom economy, low production cost and the like.

MMA is synthesized by an aldol condensation reaction of methyl propionate and formaldehyde, which belongs to an acid-base catalysis process. In this process, a silicon dioxide loaded metal cesium catalyst has good catalytic performance, but has a problem of poor stability of the catalyst, and furthermore for the conventional analysis method, it is slow in feedback, difficult to quickly judge the reaction state and adjust related parameters, which is not beneficial to the stability of production.

In summary, the conventional methods for stabilizing MMA production and improving reaction efficiency have been discussed, but it lacks a method for accurately controlling the reaction process and the post-treatment process, and does not refer to the subsequent treatment method of the reaction solution and re-use of the material stream.

SUMMARY

According to various embodiments of the present disclosure, a method and an apparatus for preparing methyl methacrylate are provided. In this preparation method, a yield of methyl methacrylate product is high, the material streams can be circulated, and the waste is small. Furthermore, the preparation apparatus can operate stably and efficiently.

A method for preparing methyl methacrylate is provided, including the following steps:

step (1), mixing a ninth material stream with a sixth material stream and a twelfth material stream to obtain a tenth material stream, performing an aldol condensation reaction in a reactor to obtain a first material stream, wherein the ninth material stream is methyl propionate and a catalyst is provided in the reactor;

step (2), heating and distilling the first material stream through a first distillation equipment, obtaining a third material stream from a bottom outlet of the first distillation equipment and a sixteenth material stream from a top outlet of the first distillation equipment, heating and distilling the sixteenth material stream through a second distillation device, obtaining a second material stream from a bottom outlet of the second distillation equipment and an eleventh material stream from a top outlet of the second distillation equipment, wherein the third material stream is a crude product of methyl methacrylate;

step (3), mixing a eleventh material stream with a fifteenth material stream and a seventh material stream to obtain a fourth material stream, heating and distilling the fourth material stream and the second material stream through a third distillation equipment, obtaining a sixth material stream from a bottom outlet of the third distillation equipment and a twelfth material stream from a top outlet of the third distillation equipment, circulating the sixth material stream and the twelfth material stream to step (1) for preparing the tenth material stream, obtaining a thirteenth material stream from a side outlet of the third distillation equipment, obtaining a fifth material stream and a fourteenth material stream through a phase splitting of the thirteenth material stream, circulating the fourteenth material stream to the third distillation equipment, wherein the fifteenth material stream is a formalin solution; and step (4), heating and distilling the fifth material stream through a fourth distillation equipment, obtaining a seventh material stream from a top outlet of the fourth distillation equipment, circulating the seventh material stream to step (3) to prepare the fourth material stream, and obtaining an eighth material stream from a bottom outlet of the fourth distillation equipment.

In an embodiment, reaction conditions of the aldol condensation reaction includes: a reaction temperature is in a range of 100° C. to 500° C., a pressure in the reactor is in a range of 0.2 MPa to 0.6 MPa, a molar ratio of the methyl propionate to formaldehyde is in a range of 5.0:1 to 10.0:1, a molar ratio of the formaldehyde to water is in a range of 5.0:1 to 20.0:1, and a hourly space velocity of the tenth material stream is in a range of 1 $h^{-1}$ to 1000 $h^{-1}$.

In an embodiment, the catalyst comprises a mesoporous material, a sub-nanometer cluster additive and an active component, the sub-nanometer cluster additive and the active component are loaded on the mesoporous material, the sub-nanometer cluster additive is selected from the group consisting of transition metal oxide, metalloid oxide, main group metal oxide, and any combination thereof, and the active component is an alkali metal, an alkaline earth metal, or any combination thereof.

In an embodiment, a mass fraction of the sub-nanometer cluster additive in the catalyst is in a range of 0.5% to 3.5% and a mass fraction of the active component in the catalyst is in a range of 5% to 12%.

In an embodiment, step (1) further includes monitoring a content of formaldehyde and/or methyl methacrylate in the first material stream online by an online Raman spectrum detection method, and adjusting a feed ratio, a reaction temperature, a reaction time, or any combination thereof, to assure that the content of formaldehyde in the first material stream is less than 0.5% in weight.

In an embodiment, step (1) further includes monitoring contents of formaldehyde, methyl propionate and methanol in the tenth material stream online by an online Raman spectrum detection method, and adjusting feed amounts of the ninth material stream, the sixth material stream, and the twelfth material stream, to assure that the content of formaldehyde in the tenth material stream is less than 8% in weight and a molar ratio of methyl propionate to methanol in the tenth material stream is in a range of 1.0:1 to 2.0:1.

In an embodiment, step (2) further includes monitoring a content of formaldehyde in the third material stream and a content of methyl methacrylate in the second material stream online by an online Raman spectrum detection method, and adjusting a reaction temperature in the reactor, a reaction time, reflux ratios, recovery rates and evaporation amounts of the first distillation equipment and the second distillation equipment, or any combination thereof, to ensure that the content of methyl methacrylate in the second material stream is less than 1% in weight and the content of formaldehyde in the third material stream is less than 200 ppm.

In an embodiment, step (3) further includes monitoring contents of formaldehyde in the fifth material stream and the sixth material stream online by an online Raman spectrum detection method, monitoring a content of water in the sixth material stream offline, and adjusting a feed ratio, a reflux ratio, a recovery rate, and an evaporation rate of the third distillation equipment, a temperature of the phase splitting, or any combination thereof, to assure that the content of water in the sixth material stream is less than 2% in weight, the content of formaldehyde in the sixth material stream is equal to or greater than 10% in weight, a molar ratio of methanol to formaldehyde in the sixth material stream is in a range of 0.1:1 to 0.8:1, and the content of formaldehyde in the fifth material stream is less than 3% in weight.

In an embodiment, the content of water in the sixth material stream is measured offline by a Karl Fischer method and a detection frequency is in a range of 30 minutes to 60 minutes.

In an embodiment, step (3) further includes monitoring contents of formaldehyde and methanol in the fourth material stream online by an online Raman spectrum detection method, and adjusting feed amounts of the eleventh material stream, the fifteenth material stream, and the seventh material stream, to assure that a molar ratio of methanol to formaldehyde in the fourth material stream is in a range of 0.6:1 to 1.2:1.

In an embodiment, in step of heating and distilling the fourth material stream and the second material stream through the third distillation equipment, a ratio of a mass flow rate of the second material stream to that of the fourth material stream is in a range of 2:1 to 8:1.

In an embodiment, in the step of obtaining the fifth material stream and the fourteenth material stream through the phase splitting of the thirteenth material stream and circulating the fourteenth material stream to the third distillation equipment, a ratio of a mass flow rate of the fourteenth material stream to that of the fifth material stream is in a range of 10:1 to 100:1.

In an embodiment, step (4) further includes monitoring a content of formaldehyde in the eight material stream online by an online Raman spectrum detection method, and adjusting a pressure, a reflux ratio and an evaporation rate of the fourth distillation equipment, or any combination thereof, to ensure that the content of formaldehyde in the eight material stream is less than 200 ppm and a content of water in the seven material stream is equal to or greater than 15% in weight.

In an embodiment, a distillation temperature of the first distillation equipment is in a range of 40° C. to 180° C., and a distillation pressure of the first distillation equipment is in a range of 0.02 MPa to 0.2 MPa.

In an embodiment, a distillation temperature of the second distillation equipment is in a range of 30° C. to 150° C., and a distillation pressure of the second distillation equipment is in a range of 0.02 MPa to 0.2 MPa.

In an embodiment, a distillation temperature of the third distillation equipment is in a range of 30° C. to 150° C. and a distillation pressure of the third distillation equipment is in a range of 0.02 MPa to 0.2 MPa.

In an embodiment, a distillation temperature of the fourth distillation equipment is in a range of 100° C. to 160° C. and a distillation pressure of the fourth distillation equipment is in a range of 0.1 MPa to 1 MPa.

Furthermore, an apparatus for preparing methyl methacrylate is provided, including: a first storage tank, a second storage tank, a reactor, a decanter, a first distillation equipment, a second distillation equipment, a third distillation equipment, and a fourth distillation equipment, wherein an inlet of the reactor is connected to and in communication with an outlet of the first storage tank, an inlet of the first distillation equipment is connected to and in communication with an outlet of the reactor, an inlet of the second distillation equipment is connected to and in communication with a top outlet of the first distillation equipment, a first inlet of the third distillation equipment is connected to and in communication with a bottom outlet of the second distillation equipment, and a second inlet of the third distillation equipment is connected to and in communication with an outlet of the second storage tank, an inlet of the decanter is connected to and in communication with a side outlet of the third distillation equipment, a first outlet of the decanter is connected to and in communication with a third inlet of the third distillation equipment, and a second outlet of the decanter is connected to and in communication with an inlet of the fourth distillation equipment. Furthermore, an inlet of the first storage tank is connected to and in communication with a feed pipe of methyl propionate, a top outlet of the third distillation equipment and a bottom outlet of the third distillation equipment, an inlet of the second storage tank is connected to and in communication with a feed pipe of formalin solution, a top outlet of the second distillation equipment and a top outlet of the fourth distillation equipment respectively, a crude product of methyl methacrylate is obtained from a bottom outlet of the first distillation equipment.

In an embodiment, the apparatus further includes a vaporizer of raw material, and the vaporizer of raw material is located at a top head of the reactor.

In an embodiment, the apparatus further includes a third storage tank, and an inlet of the third storage tank is connected to and in communication with a bottom outlet of the fourth distillation equipment.

In an embodiment, the outlet of the reactor is provided with at least one online Raman spectrometer.

In an embodiment, the bottom outlet of the first distillation equipment is provided with at least one online Raman spectrometer.

In an embodiment, the bottom outlet of the second distillation equipment is provided with at least one online Raman spectrometer.

In an embodiment, the bottom outlet of the third distillation equipment is provided with at least one online Raman spectrometer.

In an embodiment, the second outlet of the decanter is provided with at least one online Raman spectrometer.

In an embodiment, the outlet of the first storage tank is provided with at least one online Raman spectrometer.

In an embodiment, the outlet of the second storage tank is provided with at least one online Raman spectrometer.

In an embodiment, the top outlet of the fourth distillation equipment is provided with at least one online Raman spectrometer.

In an embodiment, the bottom outlet of the fourth distillation equipment is provided with at least one online Raman spectrometer.

The details of one or more embodiments in the present disclosure are set forth in the drawings enclosed herein and the brief description of the drawings. Other features, purposes, and advantages of the present disclosure will become apparent from the detailed description, enclosed drawings and claims.

BRIEF DESCRIPTION OF THE DRAWINGS

To better describe and illustrate the embodiments and/or examples of the present disclosure disclosed herein, reference may be made to one or more of the drawings enclosed herein. Additional details or examples used to describe the drawings should not be deemed as limitations on the scope of any of the present disclosure, the presently described embodiments and/or examples, and the best mode of the present disclosure currently understood.

Figure 1:
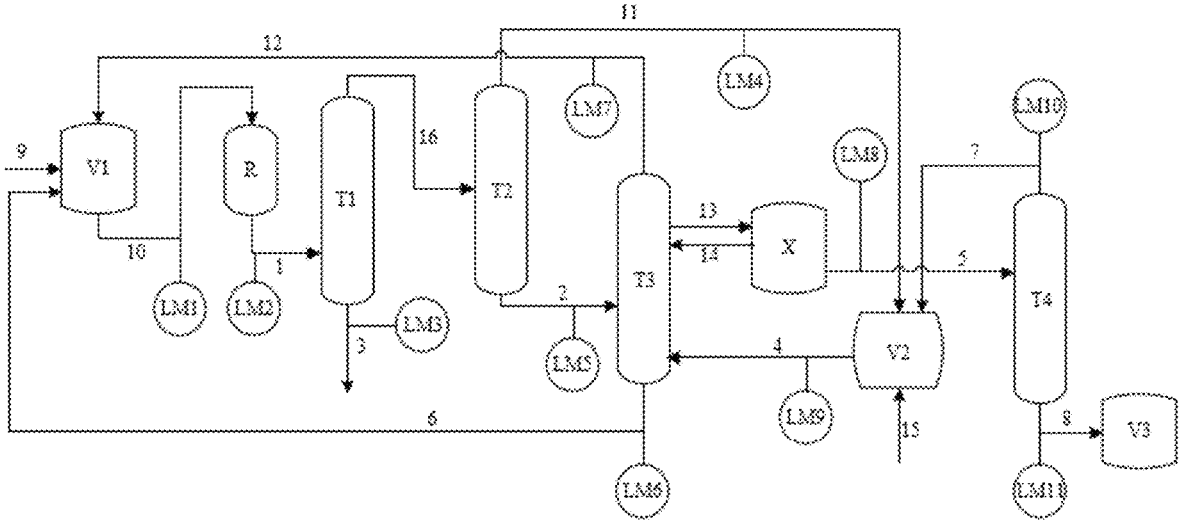
FIG. 1 is a process flow diagram of a method for preparing MMA in some embodiments.
Figure 2:
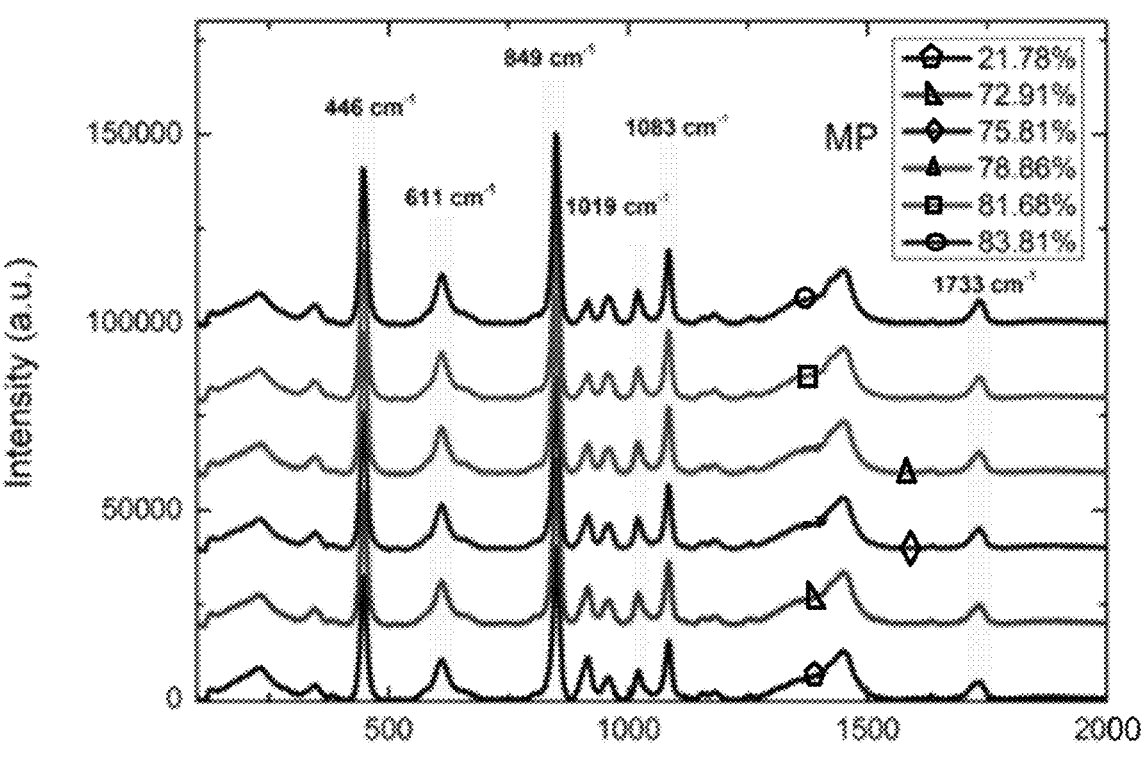
FIG. 2 is a Raman spectrogram of methyl propionate (0-2000 $cm^{-1}$).
Figure 3:
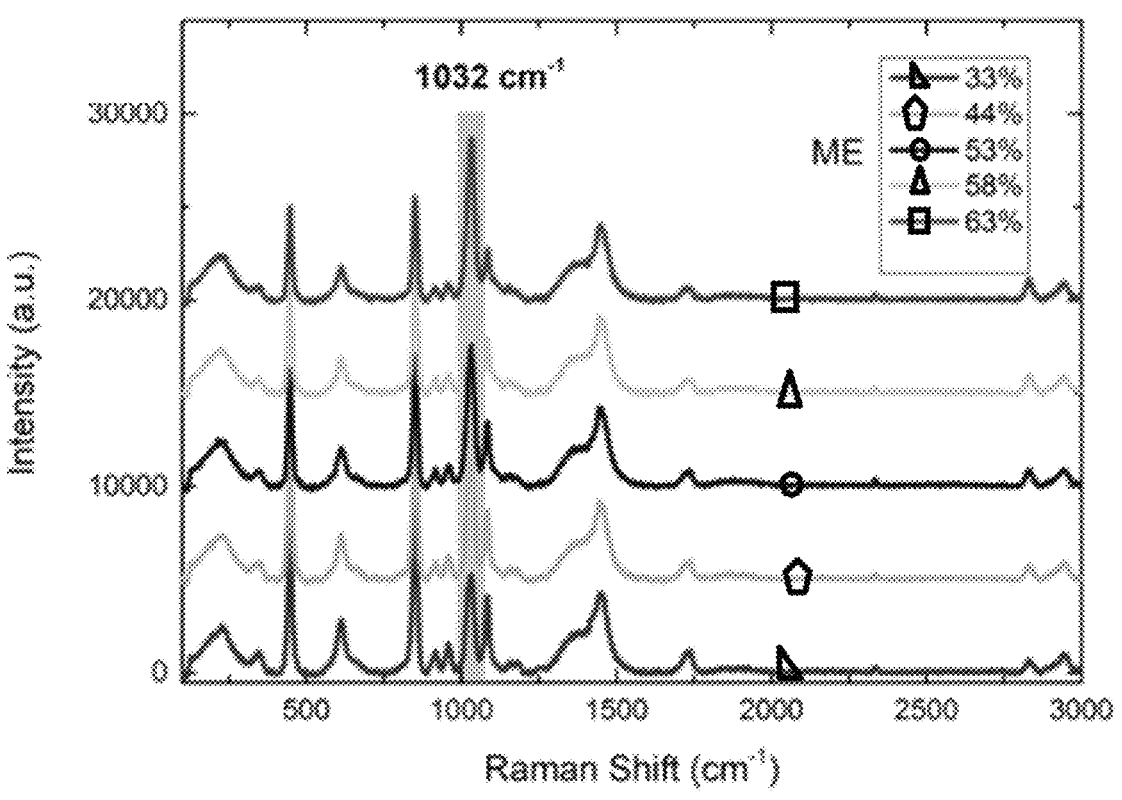
FIG. 3 is a Raman spectrogram of methanol (0-3000 $cm^{-1}$)
Figure 4:
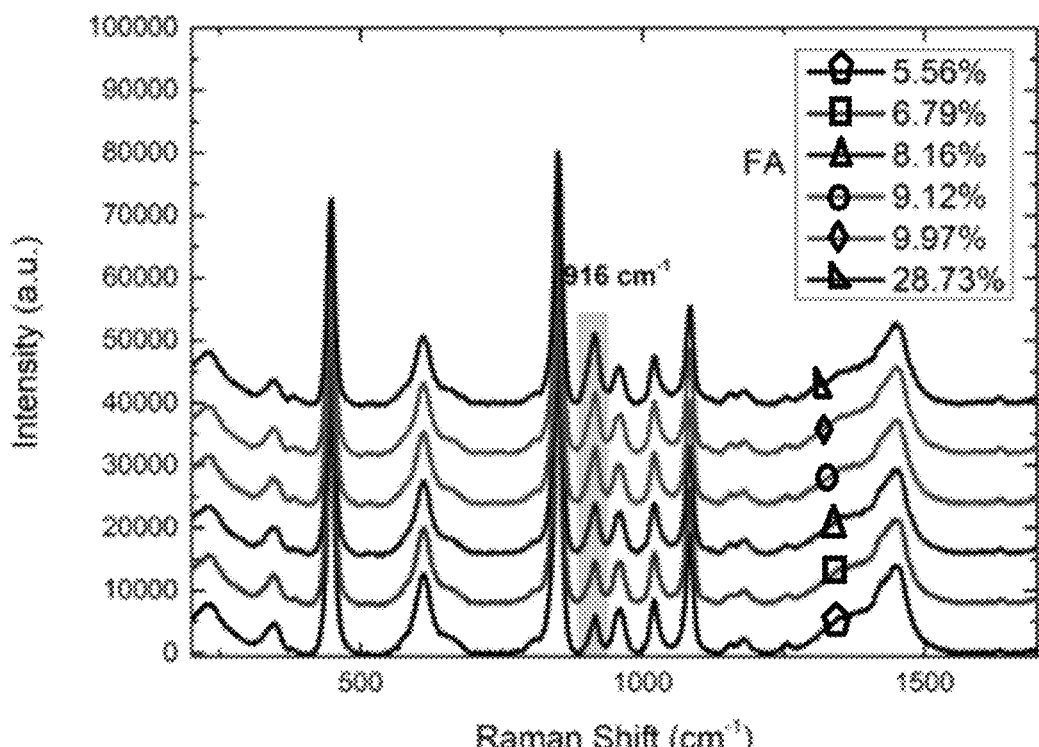
FIG. 4 is a Raman spectrogram of formaldehyde (0-2000 $cm^{-1}$)
Figure 5:
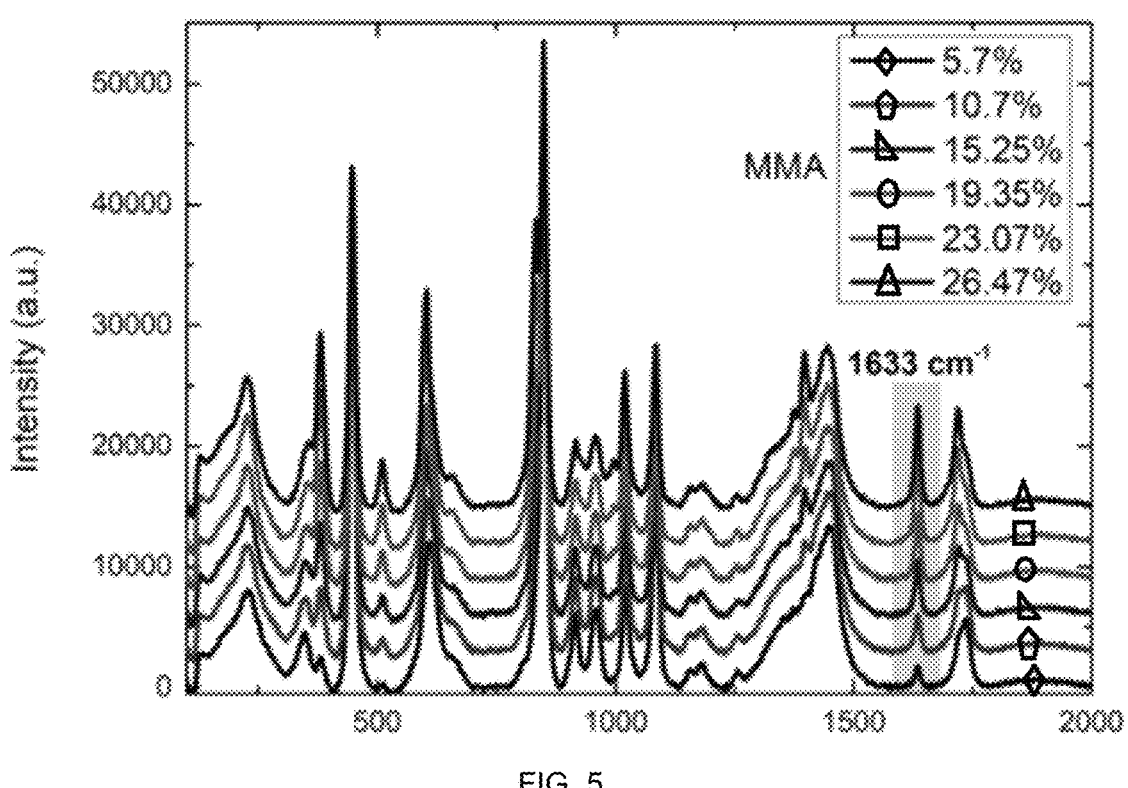
FIG. 5 is a Raman spectrogram of MMA (0-23000 $cm^{-1}$).
Figure 6:
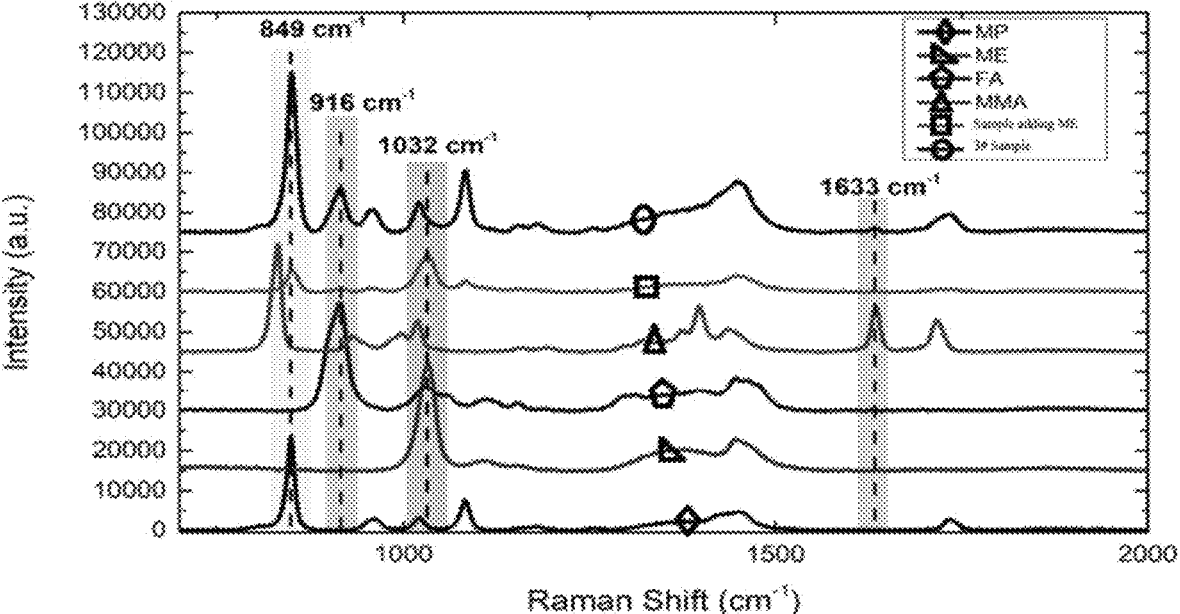
FIG. 6 is a Raman spectrogram of methyl propionate, methanol, formaldehyde, methyl methacrylate, and their mixture samples.

In these figures, 1 to 16 represent a first material stream to a sixteenth material stream respectively; T1 to T4 represent a first distillation equipment to a fourth distillation equipment respectively; V1 to V3 represent a first storage tank to a third storage tank respectively; LM1 to LM11 represent online Raman spectrometers; R represents a reactor; and X represents a decanter.

DETAILED DESCRIPTION

In the related art, a large number of studies is taken to improve a stability of a process for preparing MMA by aldol condensation. For example, a conventional method for preparing MMA by a reaction between methyl propionate and formaldehyde in a fluidized bed reactor was provided, which effectively solves the problem of rapid deactivation of the catalyst by coupling the fluidized bed reactor and the catalyst regenerator, and achieves the continuity of production. In another conventional embodiment, a device for stabilizing methyl methacrylate production was provided. The device included a plurality of reactors connected in series, a feed of methyl propionate and a plurality of feed of formaldehyde, so that an effective conversion rate of formaldehyde in the raw materials was well improved, and service life of the catalyst was prolonged; and through parallel connection of two reactors, regeneration operation on the catalyst without the process interrupt was realized, so that the whole system operated normally. It solved the problems such as unstable productivity caused by poor stability of the catalyst and high requirements of the fluidized bed on the catalyst. In another conventional embodiment, a stable method for preparing methyl methacrylate using a fluidized bed reactor was provided. In this method, methyl propionate, a formaldehyde source, methanol, water, and an oxygen-containing fluidizing gas were entered in a fluidized bed reactor after being preheated, and oxygen in the oxygen-containing fluidizing gas reacted with carbon deposition on a surface of the catalyst to form an upper oxygen-deficient region and a lower oxygen-containing region. The methyl propionate in the upper region reacted with formaldehyde to generate methyl methacrylate, and carbon deposition was formed on the catalyst. The catalyst in the lower region is in contact with oxygen to burn the carbon deposition on the surface thereof. The catalyst continuously and circularly flowed in the fluidized bed. It effectively solved the problem of rapid carbon deposition and inactivation of the catalyst in the condensation reaction of methyl propionate and formaldehyde. Formaldehyde was used in the process of preparing methyl methacrylate by reacting methyl propionate with formaldehyde, water was introduced into a formalin solution, which was harmful for the catalyst, and promoted hydrolysis reactions of methyl propionate reactants and methyl methacrylate products. In another conventional embodiment, a method for preparing formaldehyde raw material to generate methyl methacrylate was provided. The formaldehyde solution was distilled in the presence of the water azeotrope compound, so that the formaldehyde-containing product was recovered in a form of a methanol compound to obtain a formaldehyde product which was almost free of water.

The preparation method and apparatus for methyl methacrylate in the present disclosure will be further described below.

Referring to FIG. 1, a method for preparing MMA is provided, including following steps:

step (1), mixing a ninth material stream 9 with a sixth material stream 6 and a twelfth material stream 12 to obtain a tenth material stream 10, performing an aldol condensation reaction in a reactor R to obtain a first material stream 1, wherein the ninth material stream 9 is methyl propionate and a catalyst is provided in the reactor R;

step (2), heating and distilling the first material stream 1 through a first distillation equipment T1, obtaining a third material stream 3 from a bottom outlet of the first distillation equipment T1 and a sixteenth material stream 16 from a top outlet of the first distillation equipment T1, heating and distilling the sixteenth material stream 16 through a second distillation device T2, obtaining a second material stream 2 from a bottom outlet of the second distillation equipment T2 and an eleventh material stream 11 from a top outlet of the second distillation equipment T2, wherein the third material stream 3 is a crude product of methyl methacrylate;

step (3), mixing a eleventh material stream 11 with a fifteenth material stream 15 and a seventh material stream 7 to obtain a fourth material stream 4, heating and distilling the fourth material stream 4 and the second material stream 2 through a third distillation equipment T3, obtaining a sixth material stream 6 from a bottom outlet of the third distillation equipment T3 and a twelfth material stream 12 from a top outlet of the third distillation equipment T3, circulating the sixth material stream 6 and the twelfth material stream 12 to step (1) for preparing the tenth material stream 10, obtaining a thirteenth material stream 13 from a side outlet of the third distillation equipment T3, obtaining a fifth material stream 5 and a fourteenth material stream 14 through a phase splitting of the thirteenth material stream 13, circulating the fourteenth material stream 14 to the third distillation equipment T3, wherein the fifteenth material stream 15 is a formalin solution; and step (4), heating and distilling the fifth material stream 5 through a fourth distillation equipment T4, obtaining a seventh material stream 7 from a top outlet of the fourth distillation equipment T4, circulating the seventh material stream 7 to step (3) to prepare the fourth material stream 4, and obtaining an eighth material stream 8 from a bottom outlet of the fourth distillation equipment T4.

In this method, step (1) includes a step of performing the aldol condensation reaction between methyl propionate and formaldehyde in the presence of methanol and the catalyst to obtain the first material stream 1. The first material stream 1 includes methyl propionate, MMA, methanol, water, formaldehyde, methacrylic acid, and propionic acid.

In an embodiment, reaction conditions of the aldol condensation reaction includes a reaction temperature is in a range of 100° C. to 500° C., in some examples, the reaction temperature is in a range of 200° C. to 400° C.; and furthermore, in some examples, the reaction temperature is in a range of 300° C. to 380° C. A pressure in the reactor is in a range of 0.2 MPa to 0.6 MPa, and a molar ratio of methyl propionate to formaldehyde is in a range of 5.0:1 to 10.0:1, in some examples, the molar ratio of the methyl propionate to formaldehyde is in a range of 6.0:1 to 9.0:1; and furthermore in some examples, the molar ratio of the methyl propionate to formaldehyde is in a range of 7.0:1 to 8.0:1. A molar ratio of the formaldehyde to water is in a range of 5.0:1 to 20.0:1; in some examples, the molar ratio of the formaldehyde to water is in a range of 10.0:1 to 15.0:1. An hourly space velocity of the tenth material stream is in a range of 1 $h^{-1}$ to 1000 $h^{-1}$; in some examples, the hourly space velocity of the tenth material stream is in a range of 150 $h^{-1}$ to 380 $h^{-1}$; and furthermore in some examples, the hourly space velocity of the tenth material stream is in a range of 200 $h^{-1}$ to 300 $h^{-1}$.

This step further includes monitoring a content of formaldehyde and/or methyl methacrylate in the first material stream 1 online, and adjusting a feed ratio, a reaction temperature, a reaction time, or any combination thereof, to assure that the content of formaldehyde in the first material stream is less than 0.5% in weight.

In detail, it further includes real-time monitoring the first material stream 1 obtained by the aldol condensation reaction online through an online Raman spectrometer LM2, and adjusting reaction conditions of the aldol condensation reaction in time, so that selectivity of the formaldehyde to methyl methacrylate can be effectively improved to a stable level of about 82%, and a recovery cycle energy consumption of methyl propionate and equipment investment in the post-treatment process can be reduced.

Meanwhile, by real-time monitoring the content of formaldehyde in the first material stream 1, it can assure that the content of formaldehyde in the first material stream is low (less than 0.5% in weight), and effectively improve operational safety and a stability of the product composition in the first material stream 1.

In addition, in this step, the ninth material stream 9, the sixth material stream 6 and the twelfth material stream 12 can be thoroughly mixed to obtain the tenth material stream 10 in the first storage tank V1. Before entering the reactor R for the aldol condensation reaction, the tenth material stream 10 can be uniformly vaporized by a vaporization device at the top of the reactor.

Meanwhile, it further includes monitoring contents of formaldehyde, methyl propionate and methanol in the tenth material stream 10 online, and adjusting feed amounts of the ninth material stream 9, the sixth material stream 6, and the twelfth material stream 12, to assure that the content of formaldehyde in the tenth material stream 10 is less than 8% in weight and a molar ratio of methyl propionate to methanol in the tenth material stream is in a range of 1.0:1 to 2.0:1.

Specifically, the tenth material stream 10 can be real-time monitored online by an online Raman spectrometer LM1, so that the composition of the tenth material stream 10 can be accurately adjusted.

Based on the result of real-time monitoring of the tenth material stream 10 by the online Raman spectrometer LM1 and the result of real-time monitoring of the first material stream 1 by an online Raman spectrometer LM2, the related parameters of the aldol condensation reaction online can be calculated in real time, such as a conversion rate of formaldehyde, selectivity of formaldehyde to MMA, a conversion rate of methyl propionate, selectivity of methyl propionate to MMA, etc. The reaction temperature, space velocity or the opportunity of catalyst regeneration are adjusted according to the calculation results, so that the stable composition of the product can be ensured, and the stable operation of the whole reaction and application system can be realized.

In the step of performing the aldol condensation reaction, the catalyst is usually an alkali metal catalyst. In the present disclosure, the catalyst can be obtained by an impregnation method, including a mesoporous material, a sub-nanometer cluster additive and an active component. The sub-nanometer cluster additive and the active component are loaded on the mesoporous material. The sub-nanometer cluster additive is selected from the group consisting of transition metal oxide, metalloid oxide, main group metal oxide, and any combination thereof. The active component is an alkali metal, an alkaline earth metal, or any combination thereof.

In an embodiment, a mass fraction of the sub-nanometer cluster additive in the catalyst is in a range of 0.5% to 3.5% and a mass fraction of the active component in the catalyst is in a range of 5% to 12%.

The sub-nanometer cluster additive has a particle size of 0.1 nm to 1 nm, the sub-nanometer cluster additive is zirconium oxide, hafnium oxide, or any combination thereof. The active component is selected from the group consisting of potassium, rubidium, cesium, calcium, strontium, barium, and any combination thereof. The surface area of the mesoporous material is equal to or greater than 500 $m^2/g$. The mesoporous material includes mesoporous silica.

In this method, step (2) further includes a first distillation and a second distillation. In the first distillation, a distillation temperature is in a range of 40° C. to 180° C., and a pressure is in a range of 0.02 MPa to 0.2 MPa, to obtain the sixteenth material stream 16 from the top outlet of the first distillation equipment T1 and the third material stream 3 from the bottom outlet of the first distillation equipment T1. In the second distillation, the temperature is in a range from 30° C. to 150° C., and the pressure is in a range of 0.02 MPa to 0.2 MPa, to obtain the eleventh material stream 11 from the top outlet of the second distillation equipment T2 and the second material stream 2 from the bottom outlet of the second distillation equipment T2.

The second material stream 2 mainly includes an azeotropic mixture containing water. The third material stream 3 mainly includes a crude product of MMA containing low contents of formaldehyde and water. The sixteenth material stream 16 mainly includes an azeotropic mixture containing water and an azeotropic mixture containing methanol and methyl propionate. The eleventh material stream 11 mainly includes an azeotropic mixture containing methanol and methyl propionate. Furthermore, MMA with relatively high purity can be obtained by post-treatment of the material stream 3.

This step further includes monitoring a content of formaldehyde in the third material stream 3 and a content of methyl methacrylate in the second material stream 2 online, and adjusting a reaction temperature in the reactor, a reaction time, reflux ratios, recovery rates, and evaporation amounts of the first distillation equipment T1 and the second distillation equipment T2, or any combination thereof, to ensure that the content of methyl methacrylate in the second material stream 2 is less than 1% in weight and the content of formaldehyde in the third material stream 3 is less than 200 ppm.

Specifically, by real-time monitoring of the third material stream 3 through the online Raman spectrometer LM3 and the second material stream 2 through the online Raman spectrometer LM5, and adjusting the process conditions, the content of formaldehyde in the crude product of MMA can be effectively reduced, refining process of the crude product of MMA can be simplified, and the stability of MMA obtained after post-treatment can be improved.

In an embodiment, the process conditions can be further adjusted to assure that the content of formaldehyde in the third material stream 3 is less than 100 ppm, thereby improving the product stability of MMA.

In an embodiment, step (2) further includes real-time monitoring of the contents of methanol and methyl propionate in the eleventh material stream 11 by online Raman spectrometer LM4.

Due to a high content of water in the formalin solution, a dehydration and concentration process is required before the formalin solution is used for the aldol condensation reaction. Therefore, in step (3), the eleventh material stream 11 obtained in step (2) is first mixed with the fifteenth material stream 15 and the seventh material stream 7 in the second storage tank V2 to prepare the fourth material stream 4. The molar ratio of methanol to formaldehyde in the fourth material stream 4 is in a range of 0.6:1 to 1.2:1.

In an embodiment, it further includes online monitoring the contents of formaldehyde and methanol in the fourth material stream 4 and adjusting the feed rates of the eleventh material stream 11, the fifteenth material stream 15, and the seventh material stream 7, to ensure that the molar ratio of methanol to formaldehyde in the fourth material stream 4 is precisely controlled in the range of 0.6:1 to 1.2:1.

Subsequently, the fourth material stream 4 and the second material stream 2 are distilled for the third distillation in the third distillation equipment T3. In an embodiment, a ratio of a mass flow rate of the second material stream 2 to the fourth material stream 4 is in a range of 2:1 to 8:1. In some embodiments, the ratio of the mass flow rate of the second material stream 2 to the fourth material stream 4 is in a range of 3:1 to 5:1.

In the third distillation, a distillation temperature is in a range of 30° C. to 150° C., and a distillation pressure is in a range of 0.02 MPa to 0.2 MPa. Thus, the thirteenth material stream 13 is obtained from the side outlet of the third distillation equipment T3, the twelfth material stream 12 is obtained from the top outlet of the third distillation equipment T3, and the sixth material stream 6 is obtained from the bottom outlet of the third distillation equipment T3.

The sixth material stream 6 mainly includes formaldehyde, methanol, and methyl propionate. The twelfth material stream 12 mainly includes an azeotropic mixture containing methyl propionate and methanol. The thirteenth material stream 13 mainly includes an azeotropic mixture containing water. To remove water and enable full circulating of the organic phase, phase splitting of the thirteenth material stream 13 is taken in the decanter X. The resulting organic phase is used as the fourteenth material stream 14, which is then circulated to the third distillation equipment T3, heated and distilled together with the second material stream 2 and the fourth material stream 4 in the third distillation equipment T3, while the water phase is used as the fifth material stream 5.

It should be noted that, during the third distillation in the third distillation equipment T3, formaldehyde and methanol can react with each other and form a stable compound under the specific distillation conditions. As the temperature rises, the stable compound can be decomposed into formaldehyde and methanol, so that formaldehyde can be remained at the bottom of the third distillation equipment T3 while water can be discharged from the side outlet of the third distillation equipment T3, achieving effectively concentrating of the formaldehyde.

In one embodiment, in the step of obtaining the fifth material stream 5 and the fourteenth material stream 14 through the phase splitting of the thirteenth material stream 13 and circulating the fourteenth material stream 14 to the third distillation equipment T3, a ratio of a mass flow rate of the fourteenth material stream 14 to that of the fifth material stream 5 is in a range of 10:1 to 100:1.

This step further includes monitoring contents of formaldehyde in the fifth material stream 5 and the sixth material stream 6 online, monitoring a content of water in the sixth material stream 6, and adjusting a feed ratio, a reflux ratio, a recovery rate, and an evaporation rate of the third distillation equipment T3, a temperature of the phase splitting, or any combination thereof, to assure that the content of water in the sixth material stream 6 is less than 2% in weight, the content of formaldehyde in the sixth material stream 6 is equal to or greater than 10% in weight, a molar ratio of methanol to formaldehyde in the sixth material stream 6 is in a range of 0.1:1 to 0.8:1, and the content of formaldehyde in the fifth material stream 5 is less than 3% in weight.

Specifically, the contents of formaldehyde and methanol in the sixth material stream 6 are monitored in real time using an online Raman spectrometer LM6 and the amount of residual water in the sixth material stream 6 is measured by an offline detection method. At the same time, the content of formaldehyde in the fifth material stream 5 is monitored in real time by an online Raman spectrometer LM8, and the process conditions of the third distillation are adjusted in real time according to the monitoring results to achieve the optimal separation effect, so that the sixth material stream 6 and twelfth material stream 12 can be circulated to step (1) for mixing with the ninth material stream 9.

In an embodiment, the content of water in the sixth material stream 6 can be less than 0.2% in weight. The content of residual water in the sixth material stream 6 can be measured offline by a Karl Fischer method and a detection frequency is in a range of 30 minutes to 60 minutes.

In an embodiment, step (3) further includes online monitoring of contents of methanol and methyl propionate in the twelfth material stream 12 using an online Raman spectrometer LM7.

In this method, step (4) is the fourth distillation, in which the distillation temperature is in a range of 100° C. to 160° C. and the distillation pressure is in a range of 0.1 MPa to 1 MPa. Thus, the seventh material stream 7 is obtained from the top outlet of the fourth distillation equipment T4 and the eighth material stream 8 is obtained from the bottom outlet of the fourth distillation equipment T4.

The seventh material stream 7 mainly includes an azeotropic mixture of formaldehyde, methanol and water, and the eighth material stream 8 mainly includes water and a small amount of formaldehyde.

In an embodiment, step (4) further includes online monitoring of the content of formaldehyde in the eighth material stream 8 using online Raman spectrometer LM11. And in another embodiment, step (4) further includes online monitoring of the contents of formaldehyde, methyl propionate, and methanol in the seventh material stream 7 using online Raman spectrometer LM10.

Specifically, by adjusting the pressure, a reflux ratio, and an evaporation rate of the fourth distillation equipment T4, or any combination thereof, it can ensure that the content of formaldehyde in the eighth material stream 8 is less than 200 ppm and the content of water in the seventh material stream 7 is equal to or greater than 15% in weight.

As shown in FIG. 1, in this method for preparing MMA, the process can be monitored in real time using online Raman spectroscopy, and the related operating conditions can be adjusted in time. The aldol condensation reaction can be performed when methyl propionate is used as the ninth material stream 9 and the formalin solution is used as the fifteenth material stream 15. MMA can be obtained as the final product from the third material stream 3, the waste with low content of residual formaldehyde can be recovered from the eighth material stream 8, and all the other material streams can be circulated. This method can not only make full use of various material streams and improve the yield of MMA as the final product, but also simplify the waste treatment process, reduce equipment investment and costs, accurately control the amounts of formaldehyde and methyl propionate, and greatly reduce the consumption of methyl propionate.

It should be noted that, before the reaction starts, the seventh material stream 7 and the eleventh material stream 11 are first prepared and mixed with the fifteenth material stream 15 in the second storage tank, to obtain the fourth material stream 4. Then, the second material stream 2 is prepared. The second material stream 2 and the fourth material stream 4 are then heated and distilled in the third distillation equipment T3. Once the operation of the system stabilizes, the stable production process can be easily maintained by simply feeding the ninth material stream 9 and the fifteenth material stream 15.

When adjusting the related operating conditions, the reflux ratio refers to the ratio of the amount recovered from the top of the first distillation equipment T1 to the fourth distillation equipment T4 to the amount refluxed into the first distillation equipment T1 to the fourth distillation equipment T4 per unit time accordingly.

As shown in FIG. 1, the present disclosure further provides an apparatus for preparing MMA, including a first storage tank V1, a second storage tank V2, a reactor R, a decanter X, a first distillation equipment T1, a second distillation equipment T2, a third distillation equipment T3, and a fourth distillation equipment T4.

The reactor R can be a single-stage adiabatic fixed-bed reactor, a multi-stage adiabatic fixed-bed reactor, a multi-tubular fixed-bed reactor, or any combination thereof.

In this apparatus, the reactor R is configured to load catalyst and perform the aldol condensation reaction. The reactor R is provided with a top inlet and a bottom outlet. A top of the reactor R is equipped with a heating and vaporization device. The inlet of the reactor R is connected to and in communication with the outlet of the first storage tank V1, and is configured to receive the tenth material stream 10 prepared in the first storage tank V1 and perform the aldol condensation reaction in the presence of the catalyst. The outlet of the reactor R is provided at least one online Raman spectrometer LM2 for real-time monitoring of the contents of formaldehyde, methyl propionate, and MMA in the first material stream 1 which is the product of the aldol condensation reaction.

The first distillation equipment T1 is provided with a side inlet, a top outlet, and a bottom outlet. The side inlet of the first distillation equipment T1 is connected to and in communication with the outlet of the reactor R for receiving, heating, and distillation of the first material stream 1. The bottom outlet of the first distillation equipment T1 is provided with at least one online Raman spectrometer LM3 for real-time monitoring of the amount of residual formaldehyde in the third material stream 3 from the heating and distillation process.

The second distillation equipment T2 is provided with a side inlet, a top outlet, and a bottom outlet. The side inlet of the second distillation equipment T2 is connected to and in communication with the top of the first distillation equipment T1 for receiving, heating, and distillation of the sixteenth material stream 16. The bottom outlet of the second distillation equipment T2 is provided with at least one online Raman spectrometer LM5 for real-time monitoring of the content of MMA in the second material stream 2 from the heating and distillation process.

In one embodiment, the top outlet of the second distillation equipment T2 is further provided with at least one online Raman spectrometer LM4 for real-time monitoring of the contents of methanol and methyl propionate in the eleventh material stream 11 from the heating and distillation process.

The sidewall of the third distillation equipment T3 is provided with three inlets, i.e., a first inlet, a second inlet, and a third inlet. The third distillation equipment T3 is provided with a side outlet, a top outlet, and a bottom outlet. The first inlet of the third distillation equipment T3 is connected to and in communication with the bottom of the second distillation equipment T2 to receive the second material stream 2, and the second inlet of the third distillation equipment T3 is connected to and in communication with the outlet of the second storage tank V2 for receiving the fourth material stream 4 from the second storage tank V2, heating and distilling the fourth material stream 4 and the second material stream 2. The bottom outlet of the third distillation equipment T3 is provided with at least one online Raman spectrometer LM6 for real-time monitoring of the contents of formaldehyde and methanol in the sixth material stream 6 from the heating and distillation process.

In an embodiment, the top outlet of the third distillation equipment T3 is further provided with at least one online Raman spectrometer LM7 for real-time monitoring of the contents of methanol and methyl propionate in the twelfth material stream 12 from the heating and distillation process.

The inlet of the decanter X is connected to and in communication with the side outlet of the third distillation equipment T3 for receiving the thirteenth material stream 13 which is obtained by heating and distillation in the third distillation equipment T3, and then phase splitting the thirteenth material stream 13. The first outlet of the decanter X is connected to and in communication with the third inlet of the third distillation equipment T3, and is used to transfer the fourteenth material stream 14 obtained from phase splitting to the third distillation equipment T3.

To improve the efficiency of the second distillation of the second material stream 2, the fourteenth material stream 14 and the fourth material stream 4 entering the third distillation equipment T3, the twelfth material stream 12 is obtained from the top outlet of the third distillation equipment T3, and the sixth material stream 6 is obtained from the bottom outlet of the third distillation equipment T3, the position of the first inlet of the third distillation equipment T3 is higher than that of the third inlet of the third distillation equipment T3, and the position of the third inlet of the third distillation equipment T3 is higher than that of the second inlet of the third distillation equipment T3.

The fourth distillation equipment T4 is provided with a side inlet, a top outlet, and a bottom outlet. The side inlet of the fourth distillation equipment T4 is connected to and in communication with the second outlet of the decanter X for receiving, heating and distillation of the fifth material stream 5 obtained by phase splitting in the decanter X. The second outlet of the decanter X is provided with at least one online Raman spectrometer LM8 for real-time monitoring of the content of formaldehyde in the fifth material stream 5 obtained by phase splitting.

In an embodiment, the top outlet of the fourth distillation equipment T4 is provided with at least one online Raman spectrometer LM10 for real-time monitoring of the contents of formaldehyde, methyl propionate, and methanol in the seventh material stream 7 obtained from the heating and distillation process.

In an embodiment, the bottom outlet of the fourth distillation equipment T4 is provided with at least one online Raman spectrometer LM11 for real-time monitoring of the content of formaldehyde in the eighth material stream 8 obtained from the heating and distillation process.

In an embodiment, the apparatus further includes a third storage tank V3 for recycling the eighth material stream 8 which complies with the required emission standards.

The inlet of the first storage tank V1 is connected to and in communication with a feed pipe of methyl propionate and the top and bottom outlets of the third distillation equipment T3, and is configured for receiving the ninth material stream 9, and the twelfth material stream 12 and the sixth material stream 6 obtained from the heating and distillation process in the third distillation equipment T3, and mixing the ninth material stream 9, the twelfth material stream 12 and the sixth material stream 6 to obtain the tenth material stream 10.

In an embodiment, the outlet of the first storage tank V1 is provided with at least one online Raman spectrometer LM1 for real-time monitoring of the contents of formaldehyde, methanol, and methyl propionate in the tenth material stream 10.

In an embodiment, the apparatus further includes a raw material vaporizer located at a top head of the reactor. The tenth material stream 10 is fully vaporized through the raw material vaporizer before entering the reactor R for the aldol condensation reaction.

The inlet of the second storage tank V2 is connected to and in communication with a feed pipe of formalin solution, the top outlet of the second distillation equipment T2, and the top outlet of the fourth distillation equipment T4 respectively, and configured for receiving the ninth material stream 9, the eleventh material stream 11 obtained from heating and distillation in the second distillation equipment T2 and the seventh material stream 7 from heating and distillation in the fourth distillation equipment T4, and mixing the fifteenth material stream 15, the eleventh material stream 11 and the seventh stream 7 to obtain the fourth material stream 4.

In an embodiment, the outlet of the second storage tank V2 is provided with at least one online Raman spectrometer LM9 for real-time monitoring of the contents of formaldehyde and methanol in the fourth material stream 4.

In the apparatus of the present disclosure, the online Raman spectrometers can be used to monitor the process of MMA preparation in real time. It is ensured that timely adjustment of the relevant operating conditions based on the real-time monitoring results, ensuring stable and efficient operation of the highly coupled apparatus.

The method and apparatus for preparing MMA will be further described by the embodiments below.

In these embodiments, the online Raman spectra shown in FIGS. 2 to 6 were analyzed and studied, and the content of each component was determined based on the Raman spectrogram listed below:

1) the content of methyl propionate was determined based on a characteristic peak at 849 $cm^{-1}$;

2) the content of methanol was determined based on a characteristic peak at 1032 $cm^{-1}$;

3) the content of formaldehyde content was determined based on a characteristic peak at 916 $cm^{-1}$; and 4) the content of MMA was determined based on a characteristic peak at 1633 $cm^{-1}$.

Before the reaction started, the seventh material stream 7 with 2 kg/h and the eleventh material stream 11 with 4.5 kg/h were first prepared and mixed with the fifteenth material stream 15 with 5.0 kg/h in the second storage tank V2 to obtain the fourth material stream 4, and then the second material stream 2 was prepared. The second material stream 2 and the fourth material stream 4 were then heated and distilled in the third distillation equipment T3. Once the operation of the system stabilized, the stable production process was easily maintained by simply feeding the ninth material stream 9 and the fifteenth material stream 15. The catalyst loaded in the reactor R was Cs—$ZrO_2$-MCM-41 sub-nanometer cluster additives.

Example 1

4 kg of a catalyst was loaded into a reactor R, a ninth material stream 9 (methyl propionate, 6.0 kg/h) was fed into the first storage tank V1, and the fifteenth material stream 15 (including formalin solution consisting of 37% formaldehyde, 10% methanol and 53% water in weight, 5.0 kg/h) was fed into the second storage tank V2. The ninth material stream 9, the sixth material stream 6 and the twelfth material stream 12 were mixed in the first storage tank V1 to prepare the tenth material stream 10. The tenth material stream 10 prepared in the first storage tank V1, which was vaporized in the raw material vaporize before entering the reactor R for reaction, was monitored by an online Roman spectroscopy at a reaction temperature of 300° C. and under a reaction pressure of 0.2 MPa. The first material stream 1 from the reactor R was also monitored through online Raman spectroscopy, ensuring a content of formaldehyde is 0.7% in weight.

The first material stream 1 was continuously fed into the first distillation equipment T1, where the temperature at the top of the first distillation equipment was 80° C. and the temperature at the bottom of the first distillation equipment was 135° C. The third material stream 3 was discharged from the bottom outlet of the first distillation equipment T1, while the sixteenth material stream 16 was discharged from the top outlet of the first distillation equipment T1. The third material stream 3 was monitored using online Raman spectroscopy, with a content of formaldehyde being 100 ppm and a content of methyl methacrylate being 90% in weight. The sixteenth material stream 16 was continuously fed into the second distillation equipment T2, where the temperature at the top of the second distillation equipment was 74° C. and the temperature at the bottom of the second distillation equipment was 92° C. The eleventh material stream 11 was discharged from the top outlet of the second distillation equipment T2, while the second material stream 2 was discharged from the bottom outlet of the second distillation equipment T2. And the second material stream 2 was monitored using online Raman spectroscopy, and a content of MMA was 0.6% in weight.

The second material stream 2 was fed into the third distillation equipment T3 where the temperature at the top of the third distillation equipment was 45° C. and the temperature at the bottom of the third distillation equipment was 66° C. The sixth material stream 6 was discharged from the bottom outlet of the third distillation equipment T3, the twelfth material stream 12 was discharged from the top outlet of the third distillation equipment T3, and the thirteenth material stream 13 was discharged from the side outlet of third distillation equipment T3. The sixth material stream 6 was monitored using online Raman spectroscopy by an offline detection method, and a content of formaldehyde was 11.5% and a content of water was 0.12% in weight. The thirteenth material stream 13 was continuously fed into the decanter X, and the fifth material stream 5 and the fourteenth material stream 14 were obtained through phase splitting of the thirteenth material stream 13. The fifth material stream 5 was monitored using online Raman spectroscopy, and a content of formaldehyde was 3% in weight. The fourteenth material stream 14 was circulated to the third distillation equipment T3 for recycling.

The fifth material stream 5 was continuously fed into the fourth distillation equipment T4 where the temperature at the top of the fourth distillation equipment was 115° C. and the temperature at the bottom of the fourth distillation equipment was 132° C., the seventh material stream 7 was discharged from the top outlet of the fourth distillation equipment T4, and the eighth material stream 8 was discharged from the bottom outlet of the fourth distillation equipment T4. The eighth material stream 8 was monitored using online Raman spectroscopy, and a content of formaldehyde was 22 ppm.

Examples 2 to 5

The methods for preparing MMA described in Examples 2 to 5 are similar to the method for preparing MMA described in Example 1, and feed rates of various material streams and the reaction and distillation conditions in the method for preparing MMA described in Examples 1 to 5 are listed in Table 1.

TABLE 1

| Example | 9$^{th}$ stream/ kg/h | 15$^{th}$ stream/ kg/h | 7$^{th}$ stream/ kg/h | 11$^{th}$ stream/ kg/h | Reaction temperature/ ° C. | Hourly space velocity of the 10$^{th}$ stream/h$^{-1}$ | Catalyst dosage/kg | Selectivity of Formaldehyde to MMA/% | MMA yield/% | Formaldehyde concentration in V3/ppm |
|---|---|---|---|---|---|---|---|---|---|---|
| 1 | 6.0 | 5.0 | 1.5 | 3.0 | 300 | 280 | 4 | 80 | 15 | <50 |
| 2 | 6.0 | 5.0 | 1.5 | 3.0 | 340 | 220 | 4 | 76 | 13.5 | <50 |
| 3 | 10.0 | 6.0 | 1.8 | 3.6 | 300 | 380 | 6 | 82 | 15.3 | <50 |
| 4 | 12.0 | 9.0 | 2.7 | 5.4 | 380 | 150 | 6 | 73 | 12.4 | <50 |
| 5 | 14.0 | 11.0 | 3.3 | 6.6 | 320 | 200 | 6 | 81 | 14.2 | <50 |

In the present disclosure, through the appropriate design of the apparatus and the control of the method, the aldol condensation reaction can be performed when methyl propionate is used as the ninth material stream and the formalin solution is used as the fifteenth material stream. As a result, MMA is obtained as the final product from the third material stream, the waste with low content of residual formaldehyde is recovered from the eighth stream, and all the other material streams can be circulated and recycled. Therefore, this method can not only make full use of various material streams and improve the yield of MMA as the final product, but also simplify the waste treatment process and reduce equipment investment and costs.

Additionally, in the present disclosure, processes such as the aldol condensation reaction, the first distillation and second distillations can be monitored in real time using online Raman spectroscopy, and the relevant process conditions can be adjusted in time to achieve the precise control of various material streams. It can not only improve the selectivity of formaldehyde to MMA, the stability of MMA as the final product, and the stability of the recycling of material streams effectively, but also effectively improve the reaction efficiency and operational safety, ensuring stable and efficient operation of the highly coupled apparatus.

The technical features of the said embodiments can be freely combined. To keep the description concise, not all potential combinations of the technical features of the said embodiments are described herein. However, all combinations of these technical features should be considered to fall within the scope of this specification provided that there are no contradictions among them.

The said embodiments only represent several embodiments of the present disclosure, and the description thereof is relatively specific and detailed, but it should not be construed as a limitation on the scope of the present disclosure. It should be noted that the general technical personnel in this field may make several modifications and improvements without departing from the concept of the present disclosure. All such modifications and improvements are considered to fall within the scope of protection under the present disclosure. Therefore, the scope of protection granted by the present disclosure shall be determined by the appended claims.

We claim:

1. A method for preparing methyl methacrylate, comprising following steps:

step (1), mixing a ninth material stream with a sixth material stream and a twelfth material stream to obtain a tenth material stream, performing an aldol condensation reaction in a reactor to obtain a first material stream, wherein the ninth material stream is methyl propionate and a catalyst is provided in the reactor;

step (2), heating and distilling the first material stream through a first distillation equipment, obtaining a third material stream from a bottom outlet of the first distillation equipment and a sixteenth material stream from a top outlet of the first distillation equipment, heating and distilling the sixteenth material stream through a second distillation device, obtaining a second material stream from a bottom outlet of the second distillation equipment and an eleventh material stream from a top outlet of the second distillation equipment, wherein the third material stream is a crude product of methyl methacrylate;

step (3), mixing a eleventh material stream with a fifteenth material stream and a seventh material stream to obtain a fourth material stream, heating and distilling the fourth material stream and the second material stream through a third distillation equipment, obtaining a sixth material stream from a bottom outlet of the third distillation equipment and a twelfth material stream from a top outlet of the third distillation equipment, circulating the sixth material stream and the twelfth material stream to step (1) for preparing the tenth material stream, obtaining a thirteenth material stream from a side outlet of the third distillation equipment, obtaining a fifth material stream and a fourteenth material stream through a phase splitting of the thirteenth material stream, circulating the fourteenth material stream to the third distillation equipment, wherein the fifteenth material stream is a formalin solution; and step (4), heating and distilling the fifth material stream through a fourth distillation equipment, obtaining a seventh material stream from a top outlet of the fourth distillation equipment, circulating the seventh material stream to step (3) to prepare the fourth material stream, and obtaining an eighth material stream from a bottom outlet of the fourth distillation equipment.

2. The method for preparing methyl methacrylate of claim 1, wherein reaction conditions of the aldol condensation reaction comprises: a reaction temperature is in a range of 100° C. to 500° C., a pressure in the reactor is in a range of 0.2 MPa to 0.6 MPa, a molar ratio of the methyl propionate to formaldehyde is in a range of 5.0:1 to 10.0:1, a molar ratio of the formaldehyde to water is in a range of 5.0:1 to 20.0:1, and a hourly space velocity of the tenth material stream is in a range of 1 h$^{-1}$ to 1000 h$^{-1}$.

3. The method for preparing methyl methacrylate of claim 1, wherein the catalyst comprises a mesoporous material, a sub-nanometer cluster additive and an active component, the sub-nanometer cluster additive and the active component are loaded on the mesoporous material, the sub-nanometer cluster additive is selected from the group consisting of transition metal oxide, metalloid oxide, main group metal oxide, and any combination thereof, the active component is an alkali metal, an alkaline earth metal, or any combination thereof.

4. The method for preparing methyl methacrylate of claim 3, wherein a mass fraction of the sub-nanometer cluster additive in the catalyst is in a range of 0.5% to 3.5% and a mass fraction of the active component in the catalyst is in a range of 5% to 12%.

5. The method for preparing methyl methacrylate of claim 1, wherein step (1) further comprises monitoring a content of formaldehyde and/or methyl methacrylate in the first material stream online by an online Raman spectrum detection method, and adjusting a feed ratio, a reaction temperature, a reaction time, or any combination thereof, to assure that the content of formaldehyde in the first material stream is less than 0.5% in weight.

6. The method for preparing methyl methacrylate of claim 1, wherein step (1) further comprises monitoring contents of formaldehyde, methyl propionate and methanol in the tenth material stream online by an online Raman spectrum detection method, and adjusting feed amounts of the ninth material stream, the sixth material stream, and the twelfth material stream, to assure that the content of formaldehyde in the tenth material stream is less than 8% in weight and a molar ratio of methyl propionate to methanol in the tenth material stream is in a range of 1.0:1 to 2.0:1.

7. The method for preparing methyl methacrylate of claim 1, wherein step (2) further comprises monitoring a content of formaldehyde in the third material stream and a content of methyl methacrylate in the second material stream online by an online Raman spectrum detection method, and adjusting a reaction temperature in the reactor, a reaction time, reflux ratios, recovery rates and evaporation amounts of the first distillation equipment and the second distillation equipment, or any combination thereof, to ensure that the content of methyl methacrylate in the second material stream is less than 1% in weight and the content of formaldehyde in the third material stream is less than 200 ppm.

8. The method for preparing methyl methacrylate of claim 1, wherein step (3) further comprises monitoring contents of formaldehyde in the fifth material stream and the sixth material stream online by an online Raman spectrum detection method, monitoring a content of water in the sixth material stream offline, and adjusting a feed ratio, a reflux ratio, a recovery rate and an evaporation rate of the third distillation equipment, a temperature of the phase splitting, or any combination thereof, to assure that the content of water in the sixth material stream is less than 2% in weight, the content of formaldehyde in the sixth material stream is equal to or greater than 10% in weight, a molar ratio of methanol to formaldehyde in the sixth material stream is in a range of 0.1:1 to 0.8:1, and the content of formaldehyde in the fifth material stream is less than 3% in weight.

9. The method for preparing methyl methacrylate of claim 8, wherein the content of water in the sixth material stream is measured offline by a Karl Fischer method and a detection frequency is in a range of 30 minutes to 60 minutes.

10. The method for preparing methyl methacrylate of claim 1, wherein step (3) further comprises monitoring contents of formaldehyde and methanol in the fourth material stream online by an online Raman spectrum detection method, and adjusting feed amounts of the eleventh material stream, the fifteenth material stream, and the seventh material stream, to assure that a molar ratio of methanol to formaldehyde in the fourth material stream is in a range of 0.6:1 to 1.2:1.

11. The method for preparing methyl methacrylate of claim 1, wherein in step of heating and distilling the fourth material stream and the second material stream through the third distillation equipment, a ratio of a mass flow rate of the second material stream to that of the fourth material stream is in a range of 2:1 to 8:1.

12. The method for preparing methyl methacrylate of claim 1, wherein in the step of obtaining the fifth material stream and the fourteenth material stream through the phase splitting of the thirteenth material stream and circulating the fourteenth material stream to the third distillation equipment, a ratio of a mass flow rate of the fourteenth material stream to that of the fifth material stream is in a range of 10:1 to 100:1.

13. The method for preparing methyl methacrylate of claim 1, wherein step (4) further comprises monitoring a content of formaldehyde in the eight material stream online by an online Raman spectrum detection method, and adjusting a pressure, a reflux ratio, and an evaporation rate of the fourth distillation equipment, or any combination thereof, to ensure that the content of formaldehyde in the eight material stream is less than 200 ppm and a content of water in the seven material stream is equal to or greater than 15% in weight.

14. The method for preparing methyl methacrylate of claim 1, wherein a distillation temperature of the first distillation equipment is in a range of 40° C. to 180° C. and a distillation pressure of the first distillation equipment is in a range of 0.02 MPa to 0.2 MPa; and/or
a distillation temperature of the second distillation equipment is in a range of 30° C. to 150° C. and a distillation pressure of the second distillation equipment is in a range of 0.02 MPa to 0.2 MPa; and/or
a distillation temperature of the third distillation equipment is in a range of 30° C. to 150° C. and a distillation pressure of the third distillation equipment is in a range of 0.02 MPa to 0.2 MPa; and/or
a distillation temperature of the fourth distillation equipment is in a range of 100° C. to 160° C. and a distillation pressure of the fourth distillation equipment is in a range of 0.1 MPa to 1 MPa.

15. An apparatus for preparing methyl methacrylate, comprising: a first storage tank, a second storage tank, a reactor, a decanter, a first distillation equipment, a second distillation equipment, a third distillation equipment, and a fourth distillation equipment, wherein an inlet of the reactor is connected to and in communication with an outlet of the first storage tank, an inlet of the first distillation equipment is connected to and in communication with an outlet of the reactor, an inlet of the second distillation equipment is connected to and in communication with a top outlet of the first distillation equipment, a first inlet of the third distillation equipment is connected to and in communication with a bottom outlet of the second distillation equipment, and a second inlet of the third distillation equipment is connected to and in communication with an outlet of the second storage tank, an inlet of the decanter is connected to and in communication with a side outlet of the third distillation equipment, a first outlet of the decanter is connected to and in communication with a third inlet of the third distillation equipment, and a second outlet of the decanter is connected to and in communication with an inlet of the fourth distillation equipment; wherein an inlet of the first storage tank is connected to and in communication with a feed pipe of methyl propionate, a top outlet of the third distillation equipment and a bottom outlet of the third distillation equipment, an inlet of the second storage tank is connected to and in communication with a feed pipe of formalin solution, a top outlet of the second distillation equipment and a top outlet of the fourth distillation equipment respectively, a crude product of methyl methacrylate is obtained from a bottom outlet of the first distillation equipment.

16. The apparatus for preparing methyl methacrylate of claim 15, further comprising a vaporizer of raw material, wherein the vaporizer of raw material is located at a top head of the reactor.

17. The apparatus for preparing methyl methacrylate of claim 15, further comprising a third storage tank, wherein an inlet of the third storage tank is connected to and in communication with a bottom outlet of the fourth distillation equipment.

18. The apparatus for preparing methyl methacrylate of claim 15, wherein the outlet of the reactor is provided with at least one online Raman spectrometer; and/or
the bottom outlet of the first distillation equipment is provided with at least one online Raman spectrometer; and/or
the bottom outlet of the second distillation equipment is provided with at least one online Raman spectrometer; and/or
the bottom outlet of the third distillation equipment is provided with at least one online Raman spectrometer; and/or
the second outlet of the decanter is provided with at least one online Raman spectrometer; and/or
the outlet of the first storage tank is provided with at least one online Raman spectrometer; and/or the outlet of the second storage tank is provided with at least one online Raman spectrometer; and/or the top outlet of the fourth distillation equipment is provided with at least one online Raman spectrometer; and/or the bottom outlet of the fourth distillation equipment is provided with at least one online Raman spectrometer.

* * * * *